(12) United States Patent
Bidarahalli et al.

(10) Patent No.: US 6,775,834 B2
(45) Date of Patent: Aug. 10, 2004

(54) SYSTEM AND METHOD FOR FACILITATING THE COMMUNICATION OF DATA ON A DISTRIBUTED MEDICAL SCANNER/WORKSTATION PLATFORM

(75) Inventors: Phani K. Bidarahalli, Waukesha, WI (US); Michael D. Krajnak, Waukesha, WI (US); Sathish T. Chandrashekar, Karnataka (IN); Vijay K. Paladugu, Karnataka (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 487 days.

(21) Appl. No.: 09/853,116

(22) Filed: May 10, 2001

(65) Prior Publication Data

US 2002/0124119 A1 Sep. 5, 2002

Related U.S. Application Data

(60) Provisional application No. 60/272,508, filed on Mar. 1, 2001.

(51) Int. Cl.[7] .................................................. G06F 9/54
(52) U.S. Cl. ........................................ 719/328; 706/924
(58) Field of Search .......................... 709/328; 717/104, 717/108; 706/924; 719/328, 316, 315

(56) References Cited

U.S. PATENT DOCUMENTS 5,668,998 A 9/1997 Mason et al. ............... 709/328
5,835,735 A * 11/1998 Mason et al. ............... 710/107

* cited by examiner

Primary Examiner—St. John Courtenay, III
(74) Attorney, Agent, or Firm—Quarles & Brady LLP; Carl Horton

(57) ABSTRACT

A system and method is disclosed for facilitating the communication of data on a distributed medical scanner workstation platform. In one embodiment, a distributed medical scanner/workstation platform includes a first repository, a second repository, and a host on which is running an application. The host is coupled to the first and second repositories and the application is capable of communication with each of the first and second repositories. The application is in communication with each of the first and second repositories by way of an API framework, where the API framework allows the application to communicate with each of the first and second repositories as if both repositories were identical. The API framework includes a plurality of commands concerning generic communication operations between the application and any of the repositories.

20 Claims, 3 Drawing Sheets

SYSTEM AND METHOD FOR FACILITATING THE COMMUNICATION OF DATA ON A DISTRIBUTED MEDICAL SCANNER/WORKSTATION PLATFORM

CROSS REFERENCE TO RELATED APPLICATIONS

This application claims the benefit of U.S. provisional patent application Ser. No. 60/272,508, which was filed on Mar. 1, 2001 and is entitled "System and Method for Facilitating the Communication of Data on a Distributed Medical Scanner/Workstation Platform".

BACKGROUND OF THE INVENTION

The field of the invention is medical imaging methods and systems. More particularly, the invention relates to a system and method for facilitating the communication of data between applications running on a distributed medical scanner/workstation platform and repositories that can exist as part of or in communication with the scanner/workstation platform.

Conventional medical scanner/workstation platforms can include a variety of different repositories, that is, devices or subsystems that can receive, provide and store data. Such repositories, for example, can include databases, archive, networks and printers. With the increasing complexity of modern medical scanner/workstation platforms, and the increasing diversity in the types and numbers of such repositories that are employed in such platforms, the complexity in communicating information to and from such repositories on the platforms also is increased.

In particular, applications that are operating on or in communication with the medical scanner/workstation platforms must be able to communicate with the different repositories even though the different repositories operate in accordance with different communication protocols. In conventional systems, this requires that each application be aware of the type of repository that it is dealing with or needs to deal with, and also be aware of the type of data being communicated.

Additionally, more than one repository can potentially be located on a single host, or conversely multiple repositories can be located on different local or remote hosts that are in contact with one another by way of a network such as an intranet or the internet. As a result, applications must further be capable of dealing with repositories that are located at a variety of positions, that are located on the same or different hosts, or that are separated from the applications by a variety of different networking and other communication protocols (including internet and intranet protocols).

In order for applications to be able to communicate with a multiplicity of different repositories that can operate in accordance with a variety of different communication protocols and can be located at a variety of different positions, the applications require large amounts of complex programming. In particular, the applications typically must include a large number of translation programs or Application Program Interfaces (APIs) that allow for such communication with various repositories operating over various media via various communication protocols.

Designing and programming such APIs is a significant cost in the design and operation of modern distributed medical scanner/workstation platforms. The costs are particularly high insofar as, when the behavior or technology of a given repository is modified, when new repositories are added to the scanner/workstation platforms, or when the communicated data types are extended or otherwise changed, the APIs can require extensive changes in order for existing applications to remain compatible with the new/modified repositories.

Therefore, given the costs associated with the designing and programming of such APIs, it would be advantageous if a new system and method was developed for facilitating the communication of data between applications running on (or otherwise in communication with) a distributed medical scanner/workstation platform and repositories that are part of (or are otherwise in communication with) the scanner/workstation platform. Additionally, it would be advantageous if the new system and method facilitated communication with a wide variety of types of repositories, and facilitated communication of a variety of types of data via a variety of communication protocols.

Further, it would be advantageous if the new system and method facilitated communication regardless of whether different repositories (or the application programs) shared the same hosts, or operated on different hosts, including local or remote hosts. Additionally, it would be advantageous if the new system and method continued to work to facilitate communication even when additional repositories were added to the scanner/workstation platform or existing repositories were modified. Further, it would be advantageous if the new system and method were easy and relatively inexpensive to implement.

BRIEF SUMMARY OF THE INVENTION

The present invention relates to a distributed medical scanner/workstation platform that includes a first repository, a second repository, and a host on which is running an application. The host is coupled to the first and second repositories and the application is capable of communication with each of the first and second repositories. The application is in communication with each of the first and second repositories by way of an API framework, where the API framework allows the application to communicate with each of the first and second repositories as if both repositories were identical. The API framework includes a plurality of commands concerning generic communication operations between the application and any of the repositories.

The present invention further relates to, in a distributed medical scanner/workstation platform, a software framework comprising a command class, and a plurality of generalized commands being selected from the group comprising a read command, a write command, a list command, a delete command and a ping command, where each of the generalized commands inherits from the command class. The software framework further includes a session class in an association with the command class, where the session class includes at least one of the generalized commands, and where the session class further includes a submit API that allows the at least one generalized command to be executed on a repository. The software framework additionally includes a repository class in an association with the session class, where the repository class includes a connect API, an initialize API and a shutdown API.

The present invention additionally relates to a method of facilitating the communication of data on a distributed medical scanner/workstation platform including at least one host and at least two repositories. The method includes programming, on the at least one host, an API framework that includes a plurality of commands inheriting from a commands class. The plurality of commands concerns generic communication operations between an application running on the host and any of the repositories. The method additionally includes establishing a session between the application and one of the repositories, where a session class exists in association with the commands class and also in association with a repository class. The method further includes receiving from the application a data set and one of commands that is associated with the data set. The method additionally includes executing a submit API so that the data set and the one of the commands are appropriately communicated to the one of the repositories in the session. The API framework allows the application to communicate with each of the first and second repositories as if both repositories were identical.

The present invention further relates to a method of facilitating the communication of data on a distributed medical scanner/workstation platform including at least one host and a plurality of repositories of various types. The method includes providing software which recognizes at least one generalized command selected from the group comprising a read command, a write command, a delete command, a list command, and a ping command, all of which inherit from a commands class. The method additionally includes establishing a session between an application running on the host and one of the repositories. The method further includes receiving a data set from the application and, associated with the data set, the at least one generalized command. The method further includes processing the received data set and the at least one generalized command so that the received data set and the at least one generalized command can be transmitted and accepted by the one of the repositories.

DESCRIPTION OF THE PREFERRED EMBODIMENT

Figure 1:
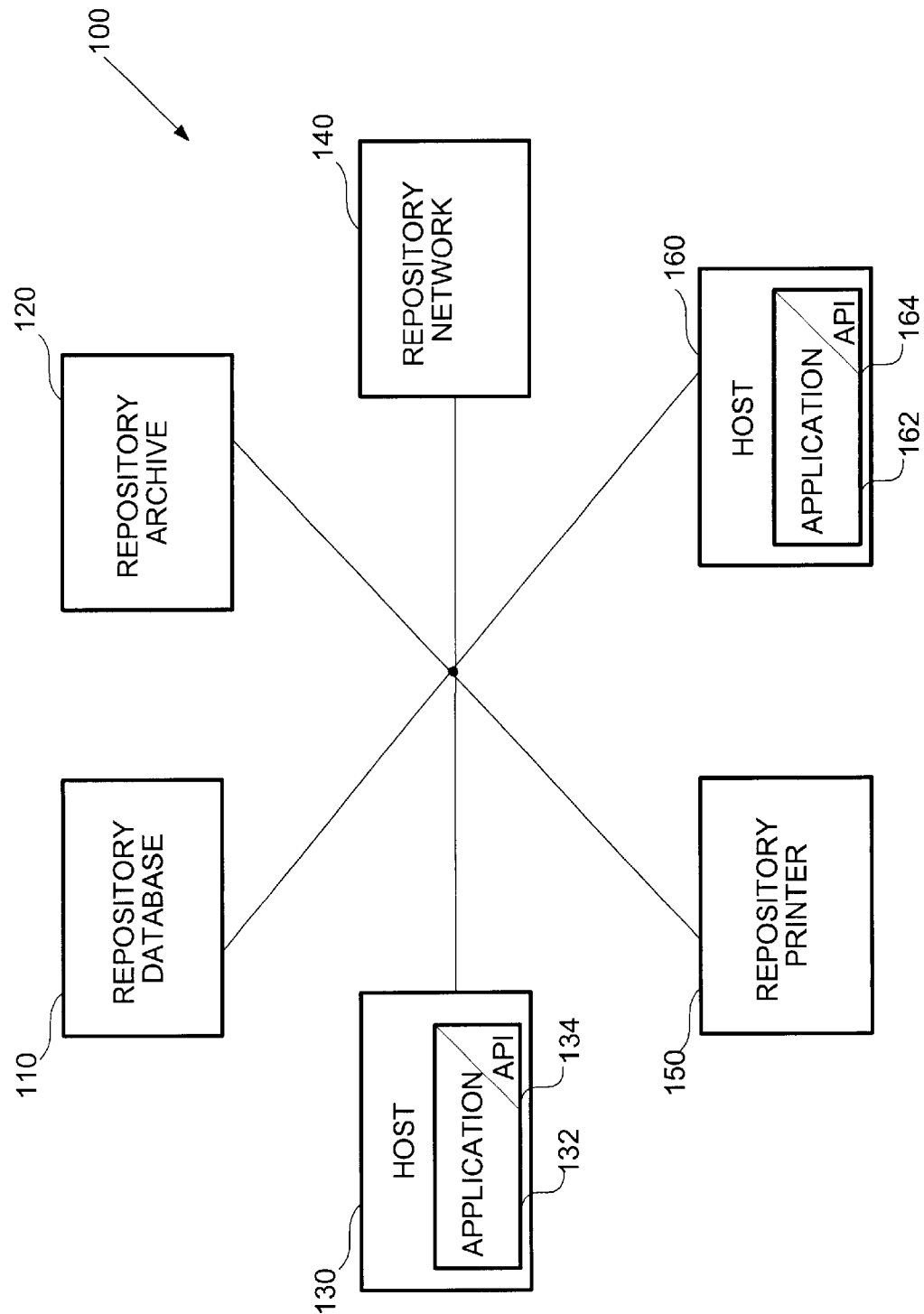
FIG. 1 is a schematic block diagram of an exemplary distributed medical scanner/workstation platform including hosts, applications and repositories, on which a new method and system for facilitating communication between such applications and repositories is implemented.

Referring to FIG. 1, an exemplary distributed medical scanner/workstation platform 100 includes one or more repositories and one or more applications running on hosts. As shown in the block diagram of FIG. 1, in one embodiment, the scanner/workstation platform 100 includes a first application 132 running on a first host 130 and a second application 162 running on a second host 160. The scanner/workstation platform 100 further includes a first repository 110, which is a database, a second repository 120, which is an archive, a third repository 140, which is a network, and a fourth repository 150, which is a printer. Although in the embodiment shown in FIG. 1, the platform 100 includes two applications 132, 162 and four different repositories 110, 120, 140 and 150, in alternate embodiments, the platform 100 can include different numbers of applications (or hosts on which the applications reside) and/or repositories. Further, the types of repositories that exist in the platform 100 can include, in alternate embodiments, a different array of repositories than that shown; for example, in one alternate embodiment, the platform could have two repositories that are printers rather than simply one, and no archive or network. The repository 140 that is a network can include a variety of different types of networks, including an internet or an intranet network. Some of the applications or repositories can be external devices that are not strictly part of the platform 100, but are in communication with the platform.

Each of the applications 132, 162 includes a respective Application Program Interface (API), respectively, APIs 134 and 164. The APIs 134, 164 allow the respective applications 132, 162 to communicate with the repositories 110, 120, 140 and 150. Effectively, the APIs 134, 164 translate between the respective communication protocols required by the repositories and the communication protocols utilized by the applications. The data communicated between the applications 132, 162 and the repositories 110, 120, 140 and 150 can include a variety of different types of data and also include meta-data, which describes what should be done with the particular data being transmitted. For example, when imaging data is transmitted the meta-data can describe whether the image data is in an 8 bit or 16 bit format.

Figure 2:
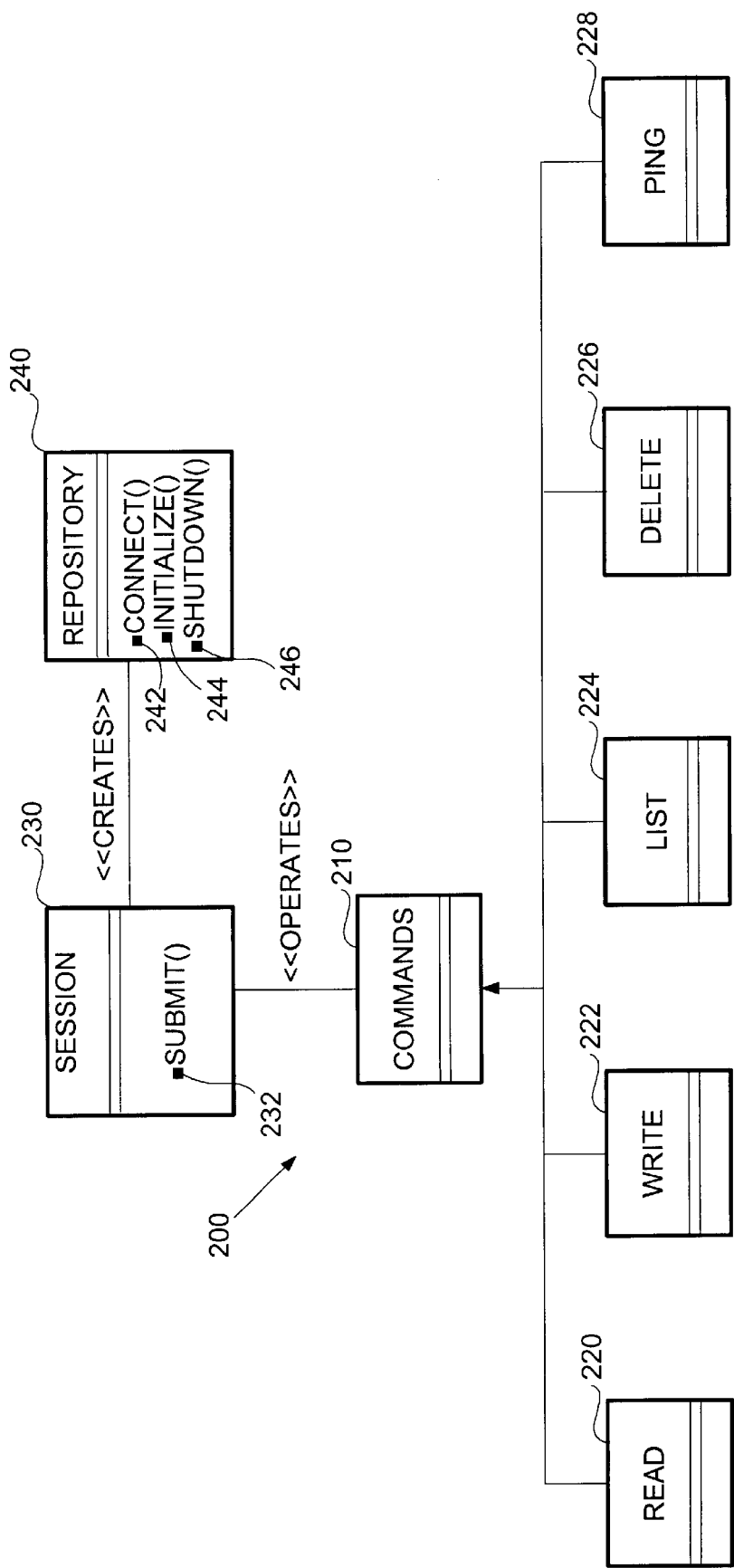
FIG. 2 is an exemplary UML software diagram showing classes and relationships of APIs employed by the new method and system of FIG. 1.

Turning to FIG. 2, the APIs 134, 164 each form a framework 200 for abstracting the repositories 110, 120, 140 and 150 so that communication between the various applications 132, 162 and the various repositories is facilitated. As shown, the framework 200 includes a set of subclasses corresponding to a set of generalized commands 220–228, each of which is in an inheritance relationship with, or inherits from, a commands class 210. The generalized commands include a read command 220, a write command 222, a list command 224, a delete command 226, and a ping command 228. All of the generalized commands 220–228 are commands that can be provided by an application in attempting to influence the operation of any one of the different types of repositories 110, 120, 140 and 150. For example, regardless of whether a particular repository is a database, archive, network, printer or other device, each repository has a particular function which corresponds to a read command, namely, a function that enables the application to read or otherwise obtain information from the respective repository.

Likewise, each repository, regardless of its type, accepts information sent to it from the application that has sent a write command. Further, each repository is able to delete information in response to a delete command, and to list the various features that are supported by the particular repository in response to a list command. Finally, each repository is able to provide status information back to an application that has provided the ping command, where a ping is a small TCP/IP packet sent to find out if a particular application/repository is alive or not. Thus, regardless of the particular type of repository that has received a given command from an application, each of the generalized commands 220–228 has a legitimate meaning and corresponds to a particular action on the part of the repository. Thus, the generalized commands 220–228 are truly general and serve to abstract the repositories. Further, the generalized commands 220–228 have a notion of transaction semantics embedded within them.

Referring still to FIG. 2, the framework 200 further includes a session class 230 and a repository class 240. The session class 230 exists to represent a particular session or communication linkage between a particular application and a particular repository. Thus, where more than one application and repository within the distributed scanner/workstation platform 100 are simultaneously communicating, multiple session classes representative of multiple sessions will typically exist simultaneously. Indeed, more than one application can be operating simultaneously on a single host and each of those applications can at the same time be in communication with a given repository in separate sessions. Each session can be considered to be the work bench on which a communication relationship between a given application and a given repository is generated, develops and proceeds.

When a command is sent from a given application to a given repository as part of a session, a particular API, namely, a submit API 232 is performed. Depending upon the situation, the submit API 232 can involve the sending of either one command and associated data to be communicated or multiple commands and one or more corresponding sets of data to be communicated. That is, in a given execution of the submit API 232, one or more commands can be performed. Further, in order to create a session in the first place, a connect API 242 and an initialize API 244 must be performed. These APIs 242, 244 are within the repository class 240. Upon the completion of a session and the ending of the communication between the application and repository of that session, a shutdown API 246 is performed, where the shutdown API is also from the repository class 240. Although the submit API 232 is designed to be able to handle and transmit the generalized commands 220–228, because some repositories have specialized additional commands apart from the generalized commands, the submit API is also in certain embodiments able to handle the transmission of these specialized commands as well.

Figure 3:
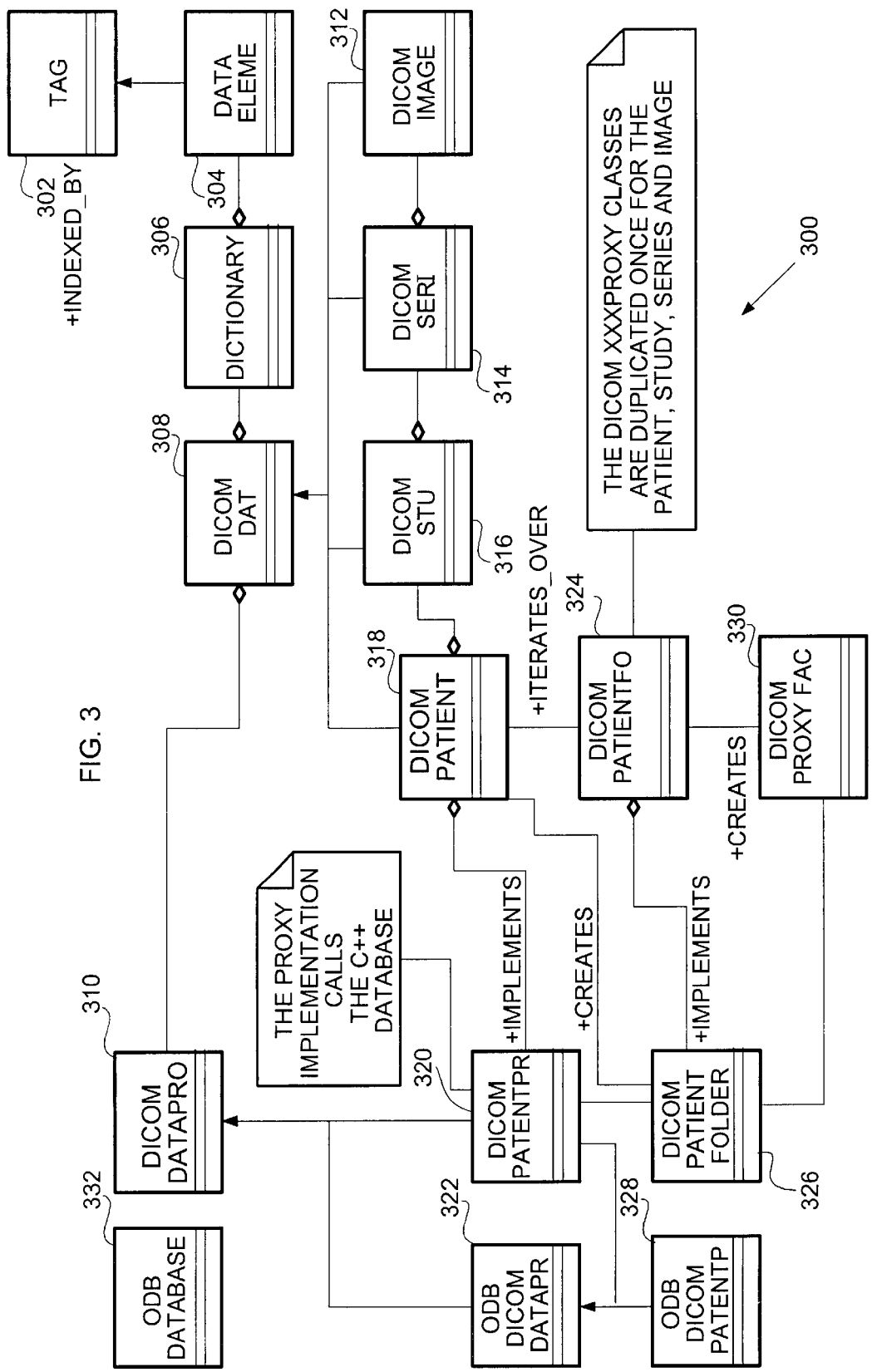
FIG. 3 is an exemplary static class diagram corresponding to the APIs of FIG. 2.

Referring to FIG. 3, an exemplary static class diagram 300 concerning data that is communicated according to the framework 200 is shown. The static class diagram 300 that is shown is particularly configured for information provided in accordance with the DICOM standard protocol for medical imaging, which is an industry-wide standard well known to those of skill in the art. Although the static class diagram 300 is configured for communication in accordance with the DICOM protocol, in alternate embodiments other static class diagrams configured for communication in accordance with other data formats can also be utilized. As shown in FIG. 3, all data is indexed by a tag class 302. A data element class 304 inherits from the tag class 302, and represents certain data. Data in the DICOM format is in a DICOM data class 308, which owns a dictionary class 306, which in turns owns the data element class 304. The DICOM data class 308 also owns a DICOM data proxy class 310.

Inheriting from the DICOM data class 308 are four different subclasses including a DICOM patient subclass 318, a DICOM study subclass 316, a DICOM series subclass 314 and a DICOM image subclass 312. The static class diagram 300 also shows that the DICOM patient subclass 318 owns the DICOM study subclass 316, which in turn owns the DICOM series subclass 314, which further owns the DICOM image subclass 312. The DICOM patient subclass 318 further owns a DICOM patient proxy subclass 320, which inherits from the DICOM data proxy class 310. A DICOM patient folder subclass 324 is in a relationship with the DICOM patient subclass 318, as well as with a DICOM proxy factor subclass 330.

The DICOM proxy factor subclass 330 is in a relationship also with a DICOM patient folder 326, which is owned by the DICOM patient folder subclass 324. The DICOM patient folder subclass 326 also is in a relationship with the DICOM patient proxy subclass 320 and the DICOM patient subclass 318. Additionally, an ODB DICOM data proxy subclass 322 inherits from the DICOM data proxy class 310, and both the DICOM patient proxy subclass 320 and an ODB DICOM patient proxy subclass 328 inherit from the ODB DICOM data proxy subclass 322. An ODB database class 332 is also included within the static class diagram.

The framework 200 allows for the abstracting of the most common APIs used in communicating with repositories, and therefore reduces the amount of knowledge that applications such as applications 132, 162 need in attempting to communicate with the various types of repositories. The framework 200 allows for repositories to handle clients (i.e., applications) that are on the same host or on different hosts, and allows repositories to provide service to multiple such client requests (i.e., in multiple sessions). The framework 200 further provides a canonical data item format and appropriate meta-data facilities that allow an application to be written in a manner that allows it to continue to operate, even if the data changes.

By providing a few basic class definitions and default communications as shown in FIG. 2, the framework 200 can be used by any of the various types of repositories such as repositories 110, 120, 140 and 150, and further can allow for the basic implementation of initialization and shutdown of a repository, and provide a basic implementation of a factory or work bench for creating sessions. The classes are distributed objects, in a sense that the classes are aware of how to marshal and unmarshal data. The static class diagram 300, which is a data item framework, provides basic classes and protocols for inspecting and updating data. The data dictionary class 306 allows an application to inspect fields and value types of a given data item. Therefore, through the implementation of a framework such as the exemplary framework 200 and a static class diagram such as diagram 300, applications on medical scanner/workstation platforms can be simpler to design and less costly, and server development also becomes faster and easier.

While the foregoing specification illustrates and describes the preferred embodiments of this invention, it is to be understood that the invention is not limited to the precise construction herein disclosed. The invention can be embodied in other specific forms without departing from the spirit or essential attributes of the invention. Accordingly, reference should be made to the following claims, rather than to the foregoing specification, as indicating the scope of the invention.

What is claimed is:

1. A distributed medical scanner/workstation platform comprising:

a first repository;

a second repository, wherein at least one of the first and second repositories is selected from the group consisting of a database and an archive;

a host on which is running an application, the host being coupled to the first and second repositories and the application being capable of communication with each of the first and second repositories; and API framework, wherein the API framework allows the application to communicate with each of the first and second repositories as if both repositories were identical, and wherein the API framework includes a plurality of commands concerning generic communication operations between the application and any of the repositories.

2. The distributed medical scanner/workstation platform of claim 1, wherein the plurality of commands concerning generic communication operations includes a read command, a write command, a list command, a delete command, and a ping command.

3. The distributed medical scanner/workstation platform of claim 1, wherein the plurality of commands inherit from a command class.

4. The distributed medical scanner/workstation platform of claim 1, wherein the command class is in association with a session class.

5. The distributed medical scanner/workstation platform of claim 4, wherein the session class includes a submit API.

6. The distributed medical scanner/workstation platform of claim 4, wherein the session class is in association with a repository class.

7. The distributed medical scanner/workstation platform of claim 6, wherein the repository class includes a connect API, an initialize API and a shutdown API.

8. The distributed medical scanner/workstation platform of claim 1, wherein each of the first repository and the second repository is selected from the group comprising a database, an archive, a network and a printer.

9. The distributed medical scanner/workstation platform of claim 1, wherein the DICOM communication protocol is employed by the application.

10. The distributed medical scanner/workstation platform of claim 9, wherein data communicated between the application and each of the repositories is indexed by a tag class.

11. The distributed medical scanner/workstation platform of claim 9, wherein data communicated between the application and each of the repositories includes a data element class that is owned by a dictionary class, which in turn is owned by a DICOM data element class.

12. The distributed medical scanner/workstation platform of claim 11, wherein the data communicated between the application and each of the repositories includes at least one of a DICOM patient subclass, a DICOM study subclass, a DICOM sentence subclass, and a DICOM image subclass, wherein the included at least one subclass inherits from the DICOM data element class.

13. In a distributed medical scanner/workstation platform, a software framework comprising:
   a command class;
   a plurality of generalized commands being selected from the group consisting of a read command, a write command, a list command, a delete command and a ping command, wherein each of the generalized commands inherits from the command class;
   a session class in an association with the command class, wherein the session class includes at least one of the generalized commands, and wherein the session class further includes a submit API that allows the at least one generalized command to be executed on a repository; and
   a repository class in an association with the session class, the repository class including a connect API, an initialize API and a shutdown API.

14. A method of facilitating the communication of data on a distributed medical scanner/workstation platform including at least one host and at least two repositories, the method comprising:
   programming, on the at least one host, an API framework that includes a plurality of commands inheriting from a commands class, the plurality of commands concerning generic communication operations between an application running on the host and any of the repositories;
   establishing a session between the application and one of the repositories, wherein a session class exists in association with the commands class and also in association with a repository class;
   receiving from the application a data set and one of commands that is associated with the data set; and
   executing a submit API so that the data set and the one of the commands are appropriately communicated to the one of the repositories in the session,
   wherein the repositories include first and second repositories and at least one of the first and second repositories is selected from the group consisting of a database and an archive, and
   wherein the API framework allows the application to communicate with each of the first and second repositories as if both repositories were identical.

15. The method of claim 14, wherein the plurality of commands includes a read command, a write command, a list command, a delete command and a ping command.

16. The method of claim 14, further comprising:
   executing a connect API and an initialize API to establish the session between the application and the one of the repositories.

17. The method of claim 14, further comprising:
   executing a shutdown API to end the session between the application and the one of the repositories after the data set and the one of the commands have been communicated.

18. The method of claim 14, wherein the executing of the submit API further includes communicating another of the commands that is associated with the data set.

19. The method of claim 14, wherein the two repositories are selected from the group comprising a database, an archive, a network and a printer.

20. A method of facilitating the communication of data on a distributed medical scanner/workstation platform including at least one host and a plurality of repositories of various types, the method comprising:
   providing software which recognizes at least one generalized command selected from the group comprising a read command, a write command, a delete command, a list command, and a ping command, all of which inherit from a commands class;
   establishing a session between an application running on the host and one of the repositories;
   receiving a data set from the application and, associated with the data set, the at least one generalized command;
   processing the received data set and the at least one generalized command so that the received data set and the at least one generalized command can be transmitted and accepted by the one of the repositories, wherein the one repository includes at least one of a database and an archive.

* * * * *